US00PP30230P2

(12) United States Plant Patent
Cain

(10) Patent No.: US PP30,230 P2
(45) Date of Patent: Feb. 26, 2019

(54) GRAPEVINE NAMED 'IFG THIRTY-THREE'

(50) Latin Name: *Vitis vinifera*
Varietal Denomination: IFG Thirty-three

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 0 days.

(21) Appl. No.: 15/732,700

(22) Filed: Dec. 18, 2017

(51) Int. Cl.
*A01H 5/08* (2018.01)

(52) U.S. Cl.
USPC ..... Plt./205
CPC ..... *A01H 5/08* (2013.01)

(58) Field of Classification Search
USPC ..... Plt./205
CPC ..... A01H 5/0812
See application file for complete search history.

(56) References Cited

U.S. PATENT DOCUMENTS

PP24,611 P3 7/2014 Cain

*Primary Examiner* — Kent L Bell

(57) ABSTRACT

This invention is a new and distinct grapevine variety denominated 'IFG Thirty-three'. The new grapevine plant is characterized by producing small to medium size broad ellipsoidal bright red berries having very crisp texture with a very mild muscat flavor and which ripens early in the season. Berries are borne on medium size clusters which are loose but well filled.

1 Drawing Sheet

Latin name of the genus and species claimed: *Vitis vinifera.*

Variety denomination: 'IFG Thirty-three'.

BACKGROUND OF THE INVENTION

The new and distinct grapevine plant described and claimed herein originated from a hand pollinated cross of IFG 02048-103-031, an unnamed seedless selection from the IFG breeding program and IFG Fourteen (U.S. Plant Pat. No. 24,611) hybridized in May 2009. The abortive seed traces were subsequently embryo cultured and the resulting 95 plants were planted in the field in April 2010. The present variety of grapevine was selected as a single plant in July 2012 and was first asexually propagated by hardwood cuttings in December 2012 near Delano, Kern County, Calif. The resulting propagules were planted during April 2013 near Delano, Kern County, Calif. and were found to reproduce true-to-type through at least two generations of asexual reproduction using hardwood cuttings and grafting onto rootstocks.

BRIEF SUMMARY OF THE INVENTION

The new grapevine 'IFG Thirty-three' is characterized by producing small to medium size broad ellipsoidal bright red berries having very crisp texture with a very mild muscat flavor and which ripens early in the season. Berries are borne on medium size clusters which are loose but well filled and require little or no gibberellin application to thin. Berries respond well to Gibberellic acid applications to increase berry size. Berries color extremely well and do not require color enhancing chemical applications to achieve good color. 'IFG Thirty-three' stores well for at least eight weeks in cold storage with stems remaining green and berries retaining their crisp texture and flavor. To the inventor's knowledge, the known variety to which the new grapevine variety is most similar is the Flame Seedless variety (unpatented). 'IFG Thirty-three' differs from 'Flame Seedless' by ripening approximately three to four days earlier, having naturally larger berry size and having a very mild muscat flavor as opposed to the neutral flavor of 'Flame Seedless'. 'IFG Thirty-three' colors more easily than 'Flame Seedless' and has not exhibited berry cracking which often occurs with 'Flame Seedless'.

'IFG thirty-three' differs from its maternal parent, IFG 02048-103-031 by producing brighter red, crisp berries that have smaller residual seed traces and a mild muscat flavor as opposed to the softer reddish black, neutral flavored fruits of IFG 02048-103-031. It differs from its pollen parent, 'IFG Fourteen', by ripening earlier, having a looser cluster, having a larger berry with a smaller residual seed trace, having a more broad ellipsoidal berry shape, and having a less intense muscat flavor.

BRIEF DESCRIPTION OF THE DRAWING

The accompanying photographic drawing in FIG. 1 illustrates in full color 'IFG Thirty-three', taken from a 4-year-old vine. The photograph was taken outdoors with indirect lighting. The colors are as nearly true as is reasonably possible in a color representation of this type. The left side of the drawing has mature leaves. A mature fruit cluster is represented in the center of the drawing along with a typical berry in cross section. A young shoot tip with tendrils can be seen on the right side of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2016 by The Royal Horticultural Society, London, England.

Throughout this specification, subjective description values conform to those set forth by the UPOV International Union for the Protection of New Varieties of Plants publication 'Grapevine *Vitis* L. Guidelines' (TG/50/9) (2008 Apr. 9).

The descriptive matter which follows pertains to 4-year-old plants of 'IFG Thirty-three' grown in the vicinity of Delano, Kern County, Calif. during 2017, and is believed to apply to plants of the variety grown under similar conditions of soil and climate elsewhere:

VINE

General:

*Vigor*.—Moderate.
*Density of foliage*.—Medium.
*Productivity*.—Moderately productive, producing about 20.9 to 31.3 kg of fruit per vine.
*Root stock*.—Own root.
*Training method*.—Typically spur pruned leaving 2 bud spurs.

Trunk:

*Trunk diameter of* 4-*year-old vines at* 30 *cm above the soil line*.—About 4.3 cm.
*Shape*.—Slender.
*Straps*.—Short, split.
*Surface texture*.—Smooth texture to slightly rough.
*Inner bark color*.—Greyed-orange: 165A.
*Outer bark color*.—The following colors were observed: Brown: N200 B and N200 C.

SHOOTS

Young shoot:

*Form of tip*.—Fully opened.
*Distribution of anthocyanin coloration of tip*.—Absent.
*Intensity of anthocyanin coloration of tip*.—Absent.
*Density of prostrate hairs of tip*.—Sparse.
*Density of erect hairs on tip*.—Absent.
*Color*.—Yellow-green: 144B.

Woody shoot (mature canes):

*Internode length*.—Medium: About 12.1 cm.
*Width at node*.—About 1.1 cm.
*Cross section*.—Elliptic.
*Surface*.—Smooth to slightly striate.
*Main color*.—The following colors were observed: Greyed-orange: 165A and 165B and 165C and 165D.
*Density of erect hairs on nodes*.—None or very sparse.
*Density of erect hairs on internodes*.—None or very sparse.

Flowering shoot:

*Vigor during flowering*.—Medium.
*Attitude during flowering on shoots not tied*.—Erect to semi-erect.
*Color*.—Dorsal side of internodes — Yellow-green: 144A, with very slight Red-purple stripes: 59A.
*Color*.—Ventral side of internodes — Yellow-green: 144A.
*Color*.—Dorsal side of nodes — Yellow-green: 144A.
*Color*.—Ventral side of nodes — Yellow-green: 144A.
*Density of prostrate hairs on nodes*.—Very sparse.
*Density of erect hairs on nodes*.—None to very sparse.
*Density of prostrate hairs on internode*.—Very sparse.
*Density of erect hairs on internode*.—None to very sparse.
*Anthocyanin coloration of buds*.—Absent.

Tendrils:

*Distribution on the shoot* (*at full flowering*).—Discontinuous.
*Length of tendril*.—Medium: About 17.0 cm.
*Thickness of tendril* 2 *cm from base*.—About 2.0 mm.
*Color*.—Yellow-green: 144B.
*Form*.—Bifurcated and trifurcated.
*Number of consecutive tendrils*.—2.

LEAVES

Young leaves:

*Color of upper surface of first four distal unfolded leaves*.—Yellow-green: 144A.
*Color of lower surface of young leaves*.—Yellow-green: 144A.
*Average intensity and color of anthocyanin coloration of six distal leaves prior to flowering*.—Absent or very weak: Red-purple: 59B.
*Density of prostrate hairs between veins* (*lower surface*).—Absent or very sparse.
*Density of prostrate hairs on veins* (*lower surface*).—Very sparse.
*Density of erect hairs between veins* (*lower surface*).—Absent.
*Density of erect hairs on veins* (*lower surface*).—Very sparse.

Mature leaves (opposite first cluster):

*Average length*.—About 10.1 cm.
*Average width*.—About 13.1 cm.
*Mature leaf size*.—Small to medium.
*Shape of blade*.—Pentagonal.
*Number of lobes*.—5.
*Blade venation*.—Palmate.
*Anthocyanin coloration of main veins on upper side of blade*.—Weak: Red-purple: 59B.
*Mature leaf profile*.—Range of profiles from involute to undulate.
*Blistering surface of blade upper surface*.—Weak.
*Leaf apex*.—Broadly acute.
*Leaf blade tip*.—In the plane of the leaf.
*Leaf margin*.—Serrate.
*Undulation of margin*.—Slight.
*Undulation of blade between main and lateral veins*.—Over entire leaf.
*Shape of teeth*.—Both sides concave.
*Length of teeth*.—Short to medium.
*Ratio length/width of teeth*.—Medium.
*Shape of upper lateral sinuses*.—Lobes strongly overlapping.
*Depth of upper lateral sinuses*.—Deep.
*General shape petiole sinus*.—Half open.
*Shape of base of upper leaf sinuses*.—U-shaped.
*Tooth at petiole sinus*.—Occasionally present.
*Density of prostrate hairs between veins on lower surface of blade*.—Very sparse.
*Density of erect hairs between veins on lower surface of blade*.—Absent.
*Density of prostrate hairs on main veins on lower surface of blade*.—Sparse.

*Density of erect hairs on main veins on lower surface of blade*.—Very sparse.
*Density of prostrate hairs on main veins on upper surface of blade*.—Sparse.
*Density of erect hairs on main veins on upper surface of blade*.—None or very sparse.
*Autumn coloration of leaves*.—Leaves can be a single color or combination of colors, in a mottled pattern or on the edges of the leaves. The following colors were observed: Greyed-yellow: 162A and 162B, Greyed-purple: 184A and 184B and 184C and 185A, Greyed-orange: 170B.

Upper surface:
*Color*.—Green: 137A.
*Anthocyanin coloration of main veins* (*upper surface*).—Absent to very weak: Red-purple: 59B.
*Color of main veins*.—Yellow-green: 145C.
*Surface appearance*.—Glossy to semi-glossy.
*Blistering surface of blade*.—Weak to medium.

Lower surface:
*Color*.—Yellow-green: 146C.
*Anthocyanin coloration of main veins* (*lower surface*).—Weak: Red-purple: 59B.
*Color of main veins*.—Yellow-green: 145D.
*Glossiness*.—Medium.
*Surface texture*.—Smooth.
*Surface appearance*.—Dull.

Petiole:
*Length*.—About 6.4 cm.
*Diameter of petiole 2 cm from blade*.—About 1.9 mm.
*Petiole color*.—The following colors were observed: Yellow-green: 144A and Red-purple: 59A.
*Length of petiole compared to middle vein*.—Slightly shorter.
*Density of prostrate hairs on petiole*.—None to very sparse.
*Density of erect hairs on petiole*.—None.

Buds:
*Bud fruitfulness*.—Basal: mostly fruitful.
*Position of first fruitful shoot on previous season cane*.—Greater than 3 nodes.
*Dormant bud length*.—About 0.6 cm.
*Dormant bud width in the proximal/distal plane*.—About 0.6 mm.
*Dormant bud color*.—The following colors were observed: Greyed-orange: 175A and 175B.
*Time of bud burst*.—Early season; about Mar. 8, 2017.

FLOWERS

General:
*Flower sex*.—Hermaphrodite.
*Length of single flower, unopened*.—About 2.6 mm.
*Width of single flower*.—Unopened: About 1.7 mm. Opened: About 6.5 mm.
*Stamen length*.—About 3.5 mm.
*Stamen count*.—Mostly 6 with a few that have 5.
*Pollen color*.—Yellow: 10B.
*Pistil length*.—About 3.0 mm.
*Pistil color*.—Yellow-green: 144A.
*Length of first inflorescence*.—Medium: About 17.3 cm long by 9.4 cm wide.
*Position of first flowering and fruiting node*.—3$^{rd}$ node (current season growth).
*Number of inflorescence per flowering shoot*.—1.1 to 2: About 1.7.
*Time of bloom*.—Early as compared with similar varieties in the growing area of Delano, Calif.
*Date of full bloom*.—About May 2, 2017.

FRUIT

General:
*Ripening period*.—Early: Approximately Jul. 20, 2017.
*Use*.—Fresh market.
*Keeping quality*.—Good, remains commercially acceptable when stored up to 8 weeks at 0° C. and high RH.
*Resistance to*.—Insects: Average typical of *Vitis vinifera* species. Diseases: Average typical of *Vitis vinifera* species.
*Refractometer test*.—Soluble solids: About 18.2 Brix.
*Brix/acid*.—About 55.2.
*Titratable acidity*.—About 0.33.
*Juice ph*.—About 3.6.
*Juice color*.—Greyed-purple: 182B.

Cluster:
*Mature cluster length* (*peduncle excluded*).—About 30.5 cm.
*Mature cluster width*.—About 16.0 cm.
*Mature cluster weight*.—About 695 g.
*Bunch density*.—Loose.
*Number of berries*.—About 197.
*Form*.—Conical.

Peduncle:
*Lignification of peduncle*.—Weak.
*Diameter of peduncle*.—About 5.5 mm.
*Length of peduncle*.—Medium: approximately 4.1 cm.
*Color of peduncle*.—Yellow-green: 144A.

Berry:
*Uniformity of size*.—Uniform to somewhat variable.
*Single berry weight*.—About 4.2 g natural; to about 5.7 g when treated with Gibberellic acid.
*Shape*.—Broad ellipsoid.
*Seeds*.—Absent.
*Cross section*.—Circular.
*Berry dimensions*.—Longitudinal axis: about 2.0 cm; horizontal axis: About 1.9 cm.
*Pedicel length*.—About 8.8 mm.
*Pedicel width*.—About 2.1 mm.
*Pedicel color*.—Yellow-green: 144C.
*Berry firmness*.—Firm.
*Particular flavor*.—Neutral to faint muscat.
*Bloom* (*cuticular wax*).—Medium.
*Berry separation from pedicel*.—Medium to somewhat easy.
*Skin color* (*without bloom*).—The following colors were observed: Greyed-purple: N186C and N186D.
*Flesh color*.—White: NN155A.

Skin:
*Thickness*.—Medium.
*Skin toughness*.—Not notable when chewing.
*Reticulation*.—Absent.
*Tenacity*.—Tenacious to flesh.

What is claimed:

1. A new and distinct variety of grapevine as herein illustrated and described.

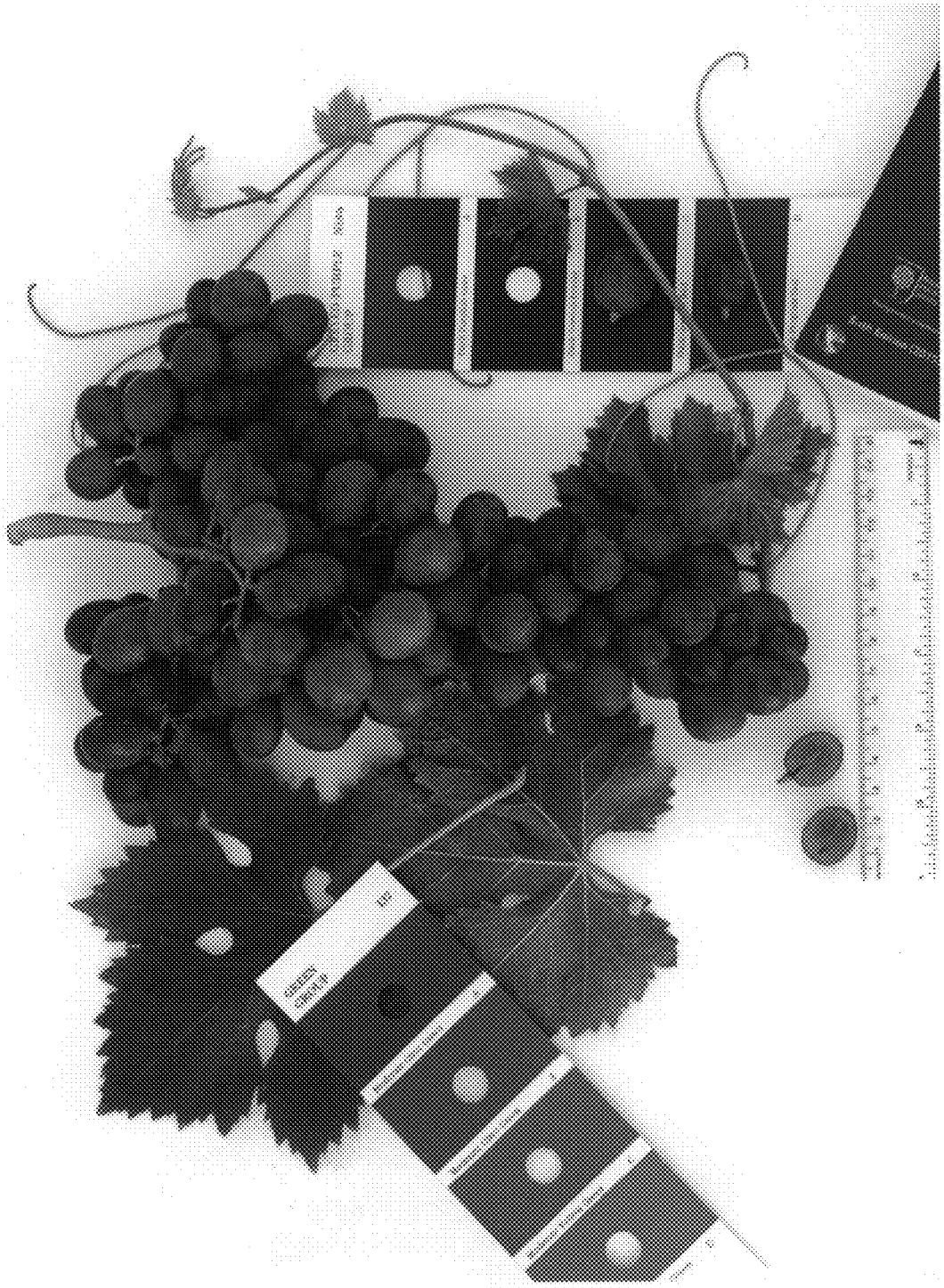

* * * * *